United States Patent [19]

Kirst et al.

[11] Patent Number: 4,459,290
[45] Date of Patent: Jul. 10, 1984

[54] C-23-MODIFIED DERIVATIVES OF OMT, PHARMACEUTICAL COMPOSITIONS AND METHOD OF USE

[75] Inventors: Herbert A. Kirst; John E. Toth, both of Indianapolis, Ind.

[73] Assignee: Eli Lilly and Company, Indianapolis, Ind.

[21] Appl. No.: 399,657

[22] Filed: Jul. 19, 1982

[51] Int. Cl.$^3$ .................... A61K 31/71; C07H 17/08
[52] U.S. Cl. .................... 424/180; 424/181; 536/7.1
[58] Field of Search .................. 424/180, 181; 536/7.1

[56] References Cited

U.S. PATENT DOCUMENTS

| | | | |
|---|---|---|---|
| 3,459,853 | 8/1969 | Gorman et al. | 424/121 |
| 4,252,898 | 2/1981 | Nash et al. | 536/7.1 |
| 4,321,361 | 3/1982 | Baltz et al. | 536/17 R |
| 4,321,362 | 3/1982 | Baltz et al. | 536/17 R |
| 4,341,770 | 7/1982 | Ose et al. | 424/181 |
| 4,341,771 | 7/1982 | Kirst et al. | 424/181 |

FOREIGN PATENT DOCUMENTS 56-122397 9/1981 Japan.
2081711 2/1982 United Kingdom.

OTHER PUBLICATIONS

Tanaka et al., "Synthesis of 4'-Deoxymycaminosyl Tylonolide", *J. Antibiotics* 34 (10), 1374–1376 (1981).
Tanaka et al., "Synthesis of Derivatives of 4'-Deoxymycaminosyl Tylonolide and Mycaminosyl Tylonolide Modified at C-23", *J. Antibiotics* 34 (10(), 1377–1380 (1981).
Tanaka et al., "Syntheses of 23-Dialkylamino Derivatives of Mycaminosyl Tylonolide and 4'-Deoxymycaminosyl Tylonolide Effective Against Gram–Negative Bacteria", *J. Antibiotics* 35 (1), 113–116 (1982).
S. Omura, "Biosynthesis of 16-Membered Macrolide Antibiotics", Japan Antibiotics Research Association 224th Scientific Meeting, May 22, 1981.
Derwent Abstract No. 12994E of Japanese Unexamined Patent 7004–999 (ZH Biseibutsu Kagaku Ken), Jan. 11, 1982.
Derwent Abstract No. 12995E of Japanese Unexamined Patent 7005–000 (ZH Biseibutsu Kagaku Ken), Jan. 11, 1982.
Derwent Abstract No. 60702D/34 of European Patent 33–433 (Schering Corp.) Nov. 9, 1979.
Tanaka et al., "Syntheses of Recyclized Macrolide Antibiotics and Related Derivatives from Mycaminosyltylonolide", *Bull. Chem. Soc. Jpn.*, 54, 3837–3845 (1981).
Matsubara et al., "Chemical Transformation of Tylosin, a 16-Membered Macrolide and its Structure–Activity Relationship", *Chem. Pharm. Bull.* 30 (1), 97–110 (1982).

Primary Examiner—Johnnie R. Brown

Attorney, Agent, or Firm—Nancy J. Harrison; Arthur R. Whale

[57] ABSTRACT

C-23-Modified derivatives of 5-O-mycaminosyl-tylonolide (OMT) of the formula:

wherein
R is chloro, fluoro, —S—R$^4$, azido, —NHR$^5$, pyridinium, or —OSO$_2$CF$_3$;
R$^1$ is hydrogen, optionally substituted C$_1$–C$_5$-alkanoyl or optionally substituted benzoyl, phenylacetyl, phenylpropionyl, phenoxyacetyl or phenylthioacetyl;
R$^2$ and R$^3$ are hydrogen, optionally substituted C$_1$–C$_5$-alkanoyl or optionally substituted benzoyl, phenylacetyl or phenylpropionyl;
R$^4$ is hydrogen, optionally substituted C$_1$–C$_6$-alkyl, cyclohexyl, C$_1$–C$_5$ alkanoyl, optionally substituted phenyl or benzyl, or an optionally substituted heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; and
R$^5$ is hydrogen or an acyl group selected from optionally substituted C$_1$–C$_5$-alkanoyl, optionally substituted benzoyl, phenylacetyl, or phenylpropionyl or optionally substituted phenylglycyl or phenylalanyl;

and of the formula:

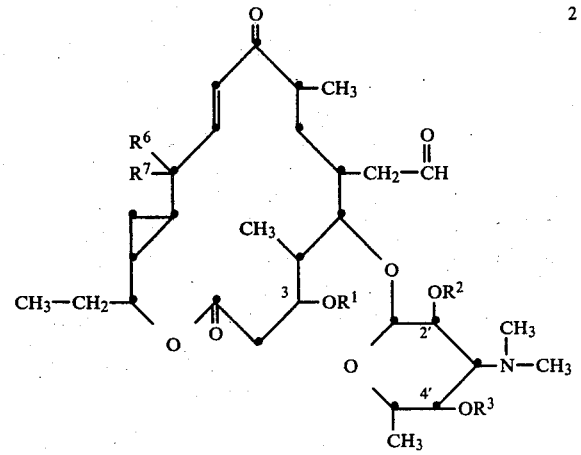
wherein:
R[6] and R[7] together form a $CH_2=$ group or
R[6] is R[8]O— and R[7] is methyl;
R[8] is $C_1$–$C_4$-alkyl, benzyl or phenethyl; and
R[1], R[2] and R[3] are as defined in formula 1;
and salts thereof are useful antibiotics or intermediates to antibiotics.
43 Claims, No Drawings

C-23-MODIFIED DERIVATIVES OF OMT, PHARMACEUTICAL COMPOSITIONS AND METHOD OF USE

SUMMARY OF THE INVENTION

This invention relates to C-23-modified derivatives of 5-O-mycaminosyl tylonolide (OMT) having formula 1:

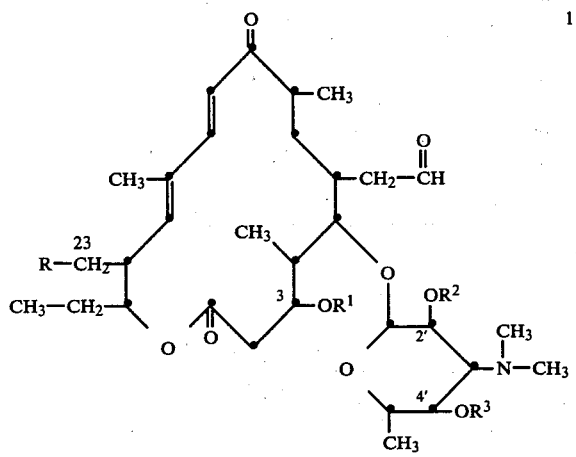

wherein:

R is chloro, fluoro, —S—$R^4$, azido, —$NHR^5$, pyridinium, or —$OSO_2CF_3$;

$R_1$ is hydrogen, optionally substituted $C_1$–$C_5$-alkanoyl or optionally substituted benzoyl, phenylacetyl, phenylpropionyl, phenoxyacetyl or phenylthioacetyl;

$R_2$ and $R_3$ are hydrogen, optionally substituted $C_1$–$C_5$-alkanoyl or optionally substituted benzoyl, phenylacetyl or phenylpropionyl;

$R^4$ is hydrogen, optionally substituted $C_1$–$C_6$-alkyl, cyclohexyl, $C_1$–$C_5$-alkanoyl, optionally substituted phenyl or benzyl, or an optionally substituted heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; and $R^5$ is hydrogen or an acyl group selected from optionally substituted $C_1$–$C_5$-alkanoyl, optionally substituted benzoyl, phenylacetyl, or phenylpropionyl or optionally substituted phenylglycyl or phenylalanyl;

and to the acid addition salts of these compounds. This invention also relates to C-23-modified derivatives of OMT having formula 2:

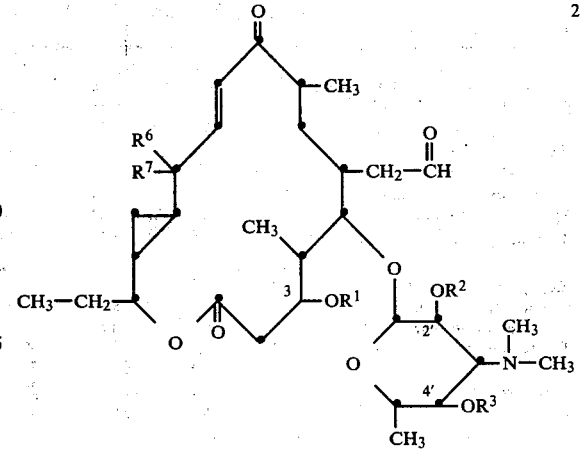

wherein:

$R^6$ and $R^7$ together form a $CH_2=$ group or $R^6$ is $R^8O—$ and $R^7$ is methyl;

$R^8$ is $C_1$–$C_4$-alkyl, benzyl or phenethyl; and $R^1$, $R^2$ and $R^3$ are as defined in formula 1;

and to the acid addition salts of these compounds. The compound of formula 2 wherein $R^6$ and $R^7$ together are $CH_2=$ and $R^1$, $R^2$ and $R^3$ are hydrogen will be called the "elimination-rearrangement product".

The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to C-23-modified derivatives of OMT and to their acid addition salts. This invention also relates to methods of treating certain infections with, methods of promoting growth in animals with, and pharmaceutical compositions comprising the specified derivatives of OMT and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

OMT is an antibiotic described by M. Gorman and R. B. Morin in U.S. Pat. No. 3,459,853, issued on Aug. 5, 1969. The structure of OMT is shown in formula 3:

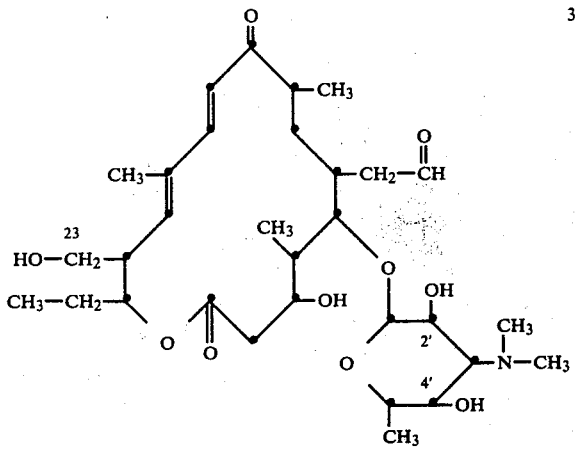

Displacement of the 23-hydroxyl group of OMT provides the derivatives of formula 1 of this invention. Displacement is accomplished by converting the 23-hydroxyl group to a suitable leaving group, such as triflate, and then displacing the leaving group with an appropriate nucleophile under suitable conditions.

The derivative of formula 2 wherein $R^6$ and $R^7$ together are methylene and $R^1$, $R^2$ and $R^3$ are hydrogen (the elimination-rearrangement product) is a by-product of the displacement reaction. The derivatives of formula 2 wherein $R^6$ is $R^8O-$ and $R^7$ is methyl are obtained by treating the 23-O-triflate derivative with the appropriate alcohol.

The derivatives of this invention generally have greater antibiotic potency than does OMT itself, as measured by minimal inhibitory concentration (MIC) values against representative gram-positive and gram-negative bacteria and Mycoplasma species.

The main group of C-23-modified derivatives of OMT of this invention are compounds of formula 1

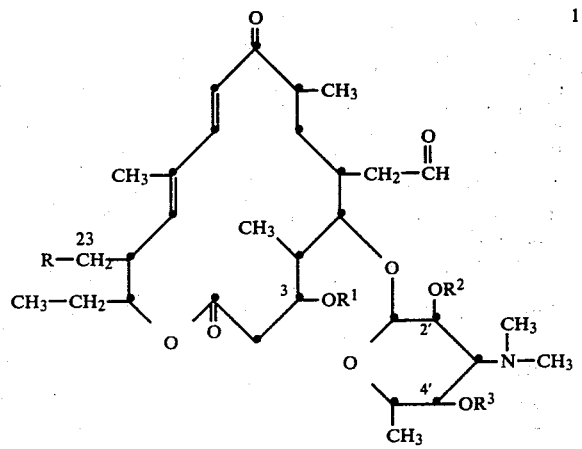

wherein:

R is chloro, fluoro, $-S-R^4$, azido, $-NHR^5$, pyridinium, or $-OSO_2CF_3$;

$R^1$ is hydrogen, optionally substituted $C_1-C_5$-alkanoyl or optionally substituted benzoyl, phenylacetyl, phenylpropionyl, phenoxyacetyl or phenylthioacetyl;

$R^2$ and $R^3$ are hydrogen, optionally substituted $C_1-C_5$-alkanoyl or optionally substituted benzoyl, phenylacetyl or phenylpropionyl;

$R^4$ is hydrogen, optionally substituted $C_1-C_6$-alkyl, cyclohexyl, $C_1-C_5$-alkanoyl, optionally substituted phenyl or benzyl, or an optionally substituted heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; and $R^5$ is hydrogen or an acyl group selected from optionally substituted $C_1-C_5$-alkanoyl, optionally substituted benzoyl, phenylacetyl, or phenylpropionyl, or optionally substituted phenylglycyl or phenylalanyl.

This invention also relates to C-23-modified derivatives of OMT having formula 2:

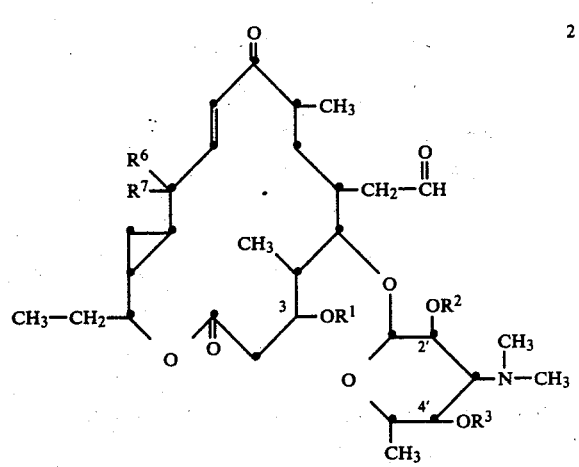

wherein:

$R^6$ and $R^7$ together form a $CH_2=$ group or $R^6$ is $R^8O-$ and $R^7$ is methyl;

$R^8$ is $C_1-C_4$-alkyl, benzyl or phenethyl; and $R^1$, $R^2$ and $R^3$ are as defined in formula 1. The acid addition salts of the compounds of formula 1 and 2 are also part of this invention.

The term "$C_1-C_5$-alkanoyl" as used herein means an acyl moiety derived from a carboxylic acid containing from one to five carbon atoms. In such a moiety, the alkyl group can be straight, branched, or cyclic. When optionally substituted, this group can bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups.

The terms "optionally substituted benzoyl, phenylacetyl, phenylpropionyl, phenoxyacetyl or phenylthioacetyl", "optionally substituted benzoyl, phenylacetyl or phenylpropionyl", and "optionally substituted phenyl or benzyl" mean that the phenyl portion of the moiety is optionally substituted by from one to five halo or methyl or by from one to two methoxyl, nitro or hydroxyl groups.

The term "optionally substituted heteroaryl group" as used herein means that the heteroaryl group may have at least one suitable substituent(s) such as a $C_1-C_4$-alkyl, methoxy, ethoxy, hydroxy (or the keto tautomer)

phenyl or phenyl optionally substituted by one or more halo, methyl or methoxyl groups.

The terms "$C_1$-$C_6$-alkyl" and "$C_1$-$C_4$-alkyl" as used herein mean a straight- or branched-chain alkyl group containing from one to six or one to four carbon atoms, respectively. Such groups include methyl, ethyl, isopropyl, n-butyl, sec-butyl, isobutyl, tert-butyl, and, for the former, n-pentyl, isopentyl, n-hexyl and the like.

The term "optionally substituted phenylglycyl or phenylalanyl" means that the amino group is optionally substituted by a suitable protecting group, such as the tert-butoxycarbonyl (t-BOC) group. Such a group is an example of one which is stable under the conditions of acylation, but which can be readily removed from the derivative once it has been prepared.

The C-23-modified derivatives of this invention are prepared from OMT or from ester derivatives of OMT. The preparation of OMT is described by Gorman et al. in U.S. Pat. No. 3,459,853. OMT can also be prepared from demycinosyltylosin (DMT). DMT is an antibiotic described by Richard H. Baltz, Gene M. Wild, and Eugene T. Seno in U.S. Pat. No. 4,321,361, issued on Mar. 23, 1982. The structure of DMT is shown in formula 4:

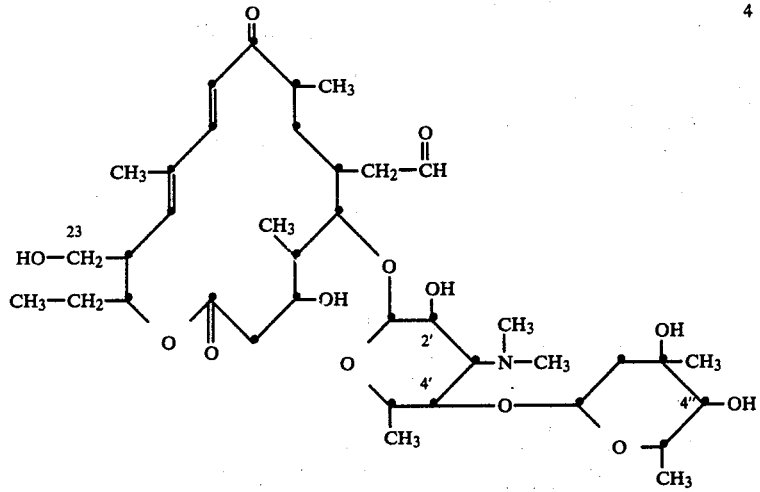

4

Preparation of the C-23-modified derivatives of OMT involves two steps. First, the 23-hydroxyl group is converted to a suitable leaving group, such groups being well known in the art. The triflate anion is a preferred leaving group. With very reactive nucleophiles, however, other leaving groups, such as the mesylate anion, the tosylate anion, iodide or bromide may also be suitable.

The second step in the preparation of the OMT derivatives involves displacement of the leaving group by the appropriate nucleophile under suitable conditions which are well exemplified in the art of displacement reactions.

The C-23 derivatives wherein R is —$NHR^5$ are prepared via the 23-azido derivative (R=$N_3$). The 23-azido derivative is first reduced to the 23-amino derivative; triphenylphosphine in aqueous tetrahydrofuran (THF) is an example of a suitable reducing agent for this purpose. The 23-amino derivative can then be selectively acylated on the amino group, using standard acylation procedures, to give those OMT derivatives wherein $R^5$ is an acyl group.

The 23-O-triflate is preferably prepared by a method analogous to that described in our co-pending application entitled METHOD OF PREPARING 23-MONO-ESTERS OF OMT AND DMT, Ser. No. 330,295, filed Dec. 14, 1981, now abandoned which is incorporated herein by reference. Using this procedure, the 23-O-triflate of OMT can be prepared without concomitant reactions at the other hydroxyl groups which are present. A similar reaction can be used to prepare the corresponding mesylate or tosylate directly.

When triflate is used as the leaving group, it is not necessary to isolate the intermediate triflate derivatives; displacement with the appropriate nucleophile can be carried out in situ. When less reactive leaving groups are used, the intermediate is sufficiently stable and may be isolated prior to the displacement reaction if so desired.

The C-23-modified derivatives of this invention wherein $R^1$, $R^2$, or $R^3$ are other than hydrogen (the ester derivatives) and R is fluoro, chloro, —S—$R^4$, azido and $NHR^5$ wherein $R^5$ is other than hydrogen may be prepared by esterifying the corresponding C-23-modified OMT derivative on the 2', 4', and/or 3-hydroxyl groups by treatment with acylating agents, using standard methods well exemplified in the art. The preparation of 2'- and 4'-O-ester derivatives of C-23-modified derivatives of OMT is accomplished by procedures similar to those described by Kirst in a copending application entitled OMT ESTER DERIVATIVES, Ser. No. 330,341, filed Dec. 14, 1981, now U.S. Pat. No. 4,401,660 which is incorporated herein by reference. 3-Ester derivatives of C-23-modified derivatives of OMT may be prepared by acylation of the 3-hydroxyl group of a 2',4'-di-O-acyl-23-modified derivative of OMT with subsequent hydrolysis of the acyl protecting groups. Conditions for hydrolysis are also described in application Ser. No. 330,341. Preferred conditions are warming or heating the compound in aqueous methanol for a suitable period of time. For esters of those C-23 derivatives wherein $R^5$ is hydrogen, acylation of the hydroxyl groups is carried out as described, supra, on an intermediate (e.g. R is azido). The desired C-23 derivative is subsequently prepared by the appropriate modification of the 23-substituent (e.g. reduction of the azide).

Alternatively, the 2'-monoesters or 2',4'-diesters of the C-23-modified derivatives of OMT can be prepared by starting with the corresponding ester derivatives of OMT, prepared as described in application Ser. No. 330,341. The 23-substituent of these esters of OMT can then be modified by the procedures described supra. It should also be noted that hydrolysis of the ester(s) of such a 2'-ester or 2',4'-diester derivative, as described supra, yields the corresponding C-23-modified derivative of OMT.

Furthermore, the C-23-modified derivatives of OMT can be prepared by acidic hydrolysis of mycarose from the corresponding C-23-modified derivative of DMT, whose synthesis is described in our copending application entitled C-23-MODIFIED DERIVATIVES OF DMT, Ser. No. 399,656, filed July 19, 1982. In addition, certain esters of C-23-modified derivatives of OMT can be obtained by hydrolysis of the corresponding C-23-modified ester derivatives of DMT, which are also described in our copending application.

The OMT derivatives of this invention form acid addition salts. These acid addition salts are also useful as antibiotics and are a part of this invention. In another aspect, such salts are useful as intermediates, for example, for separating and purifying the OMT derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

The compounds of formula 1 are preferred compounds of this invention. Pharmaceutically acceptable acid addition salts are an advantageous group of salts of this invention.

Illustrative OMT derivatives of this invention include the compounds of formula 1 listed in Tables I and II and the compound of formula 2 listed in Tables III and IV.

TABLE I

C-23 Derivatives of OMT of Formula 1

| Compound No. | R | $R^1$ (3) | $R^2$ (2') | $R^3$ (4') |
|---|---|---|---|---|
| 1 | pyridinium | H | acetyl | H |
| 2 | phenylthio | H | H | H |
| 3 | (5-methyl-1,3,4-thiadiazol-2-yl)thio | H | H | H |
| 4 | (5-methyl-1,3,4-oxadiazol-2-yl)thio | H | H | H |
| 5 | (1-methyltetrazol-5-yl)thio | H | H | H |
| 6 | (1H—5,6-dioxo-4-methyl-1,2,4-triazin-3-yl)thio | H | H | H |
| 7 | (acetyl)thio | H | H | H |
| 8 | azido | H | H | H |
| 9 | amino | H | H | H |
| 10 | N—(phenylacetyl)amino | H | H | H |
| 11 | N—(N—t-BOC—phenylglycyl)amino | H | H | H |
| 12 | N—(phenylglycyl)amino | H | H | H |
| 13 | N—[N—(t-BOC—alanyl)glycyl]amino | H | H | H |
| 14 | N—(alanylglycyl)amino | H | H | H |
| 15 | fluoro | H | H | H |

TABLE II

Illustrative C-23 Derivatives of Formula 1

| R | $R^1$ (3) | $R^2$ (2') | $R^3$ (4') |
|---|---|---|---|
| pyridinium | H | H | H |
| (1,3,4-thiadiazol-2-yl)thio | H | acetyl | acetyl |
| (1,3,4-oxadiazol-2-yl)thio | acetyl | propionyl | propionyl |
| (1-methyltetrazol-5-yl)thio | H | isovaleryl | H |
| (1H—5,6-dioxo-4-methyl-1,2,4-triazin-3-yl)thio | H | acetyl | isovaleryl |
| (acetyl)thio | acetyl | acetyl | acetyl |
| phenylthio | H | benzoyl | H |
| (3-chlorophenyl)thio | H | phenylacetyl | H |
| (3,4-dichlorophenyl)thio | H | phenylacetyl | acetyl |
| azido | H | phenylpropionyl | H |
| azido | phenoxyacetyl | acetyl | acetyl |
| amino | H | acetyl | H |
| amino | H | acetyl | acetyl |
| N—(N—t-BOC—phenylglycyl)amino | benzoyl | acetyl | acetyl |
| N—(phenylacetyl)amino | propionyl | H | H |
| N—(phenylacetyl)amino | H | phenylacetyl | phenylacetyl |
| N—(acetyl)amino | phenylacetyl | acetyl | acetyl |

TABLE III

C-23 Derivatives of OMT of Formula 2[a]

| Compound No. | $R^6, R^7$ | $R^8$ |
|---|---|---|
| 16 | $CH_2=$ | — |
| 17 | $R^8O—, CH_3—$ | $CH_3—$ |
| 18 | $R^8O—, CH_3—$ | ⌬—$(CH_2)_2$— |

[a] $R^1, R^2, R^3 = H$

TABLE IV

Illustrative C-23 Derivatives of Formula 2

| $R^6, R^7$ | $R^8$ | $R^1$ (3) | $R^2$ (2') | $R^3$ (4) |
|---|---|---|---|---|
| $CH_2=$ | — | H | acetyl | acetyl |
| $CH_2=$ | — | phenoxyacetyl | acetyl | acetyl |
| $R^8O—, CH_3—$ | $CH_3—$ | H | propionyl | propionyl |
| $R^8O—, CH_3—$ | $CH_3CH_2—$ | H | propionyl | H |
| $R^8O, CH_3—$ | n-butyl | H | H | H |
| $R^8O—, CH_3—$ | phenethyl- | H | n-butyryl | H |
| $R^8O—, CH_3—$ | benzyl | H | H | H |

The OMT derivatives of this invention inhibit the growth of pathogenic bacteria, both gram-positive and gram-negative, and Mycoplasma species. Especially noteworthy is the improved activity against gram-negative bacteria for several derivatives when compared to the activity of OMT. For example, Tables V, VI and VII show the minimal inhibitory concentrations (MIC's) at which illustrative compounds of this invention inhibit certain bacteria. The MIC's in Tables V and VI were determined by standard agar-dilution assays. The MIC's in Table VII were obtained using a conventional broth-dilution microtiter test.

TABLE V

Antibiotic Activity of OMT Derivatives[a]

| Test Organism | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Staphylococcus aureus X1.1 | 32 | 0.125 | 0.25 | 0.25 | 0.5 | 4 | 0.25 | 0.125 | 8 | 0.5 | 1 | 4 | 16 | 64 | 0.25 | 4 | 2 | 1 |
| Staphylococcus aureus V41[c] | 64 | 0.125 | 0.25 | 0.5 | 0.5 | 4 | 0.25 | 0.25 | 8 | 1 | 2 | 8 | 32 | 64 | 0.5 | 4 | 2 | 2 |
| Staphylococcus aureus X400[d] | 64 | 0.125 | 0.25 | 0.5 | 0.5 | 8 | 0.25 | 0.25 | 8 | 1 | 4 | 8 | 32 | 128 | 0.5 | 4 | 2 | 2 |
| Staphylococcus aureus S13E | 32 | 0.06 | 0.25 | 0.25 | 0.5 | 4 | 0.125 | 0.25 | 8 | 0.5 | 2 | 8 | 32 | 64 | 0.5 | 4 | 2 | 1 |
| Staphylococcus epidermidis EPI1 | 32 | 0.125 | 0.125 | 0.25 | 0.25 | 4 | 0.125 | 0.125 | 8 | 0.25 | 1 | 4 | 16 | 64 | 0.25 | 4 | 2 | 1 |
| Staphylococcus epidermidis EPI2 | 64 | 0.125 | 0.25 | 0.5 | 0.5 | 8 | 0.125 | 0.25 | 8 | 1 | 4 | 8 | 32 | 64 | 0.5 | 4 | 2 | 2 |
| Streptococcus pyogenes C203 | 32 | 0.015 | 0.125 | 0.25 | 0.25 | 1 | 0.25 | 0.125 | 2 | 0.25 | 0.5 | 0.5 | 4 | 16 | 0.125 | 1 | 1 | 1 |
| Streptococcus pneumoniae Park I | 8 | 0.06 | 0.06 | 0.06 | 0.06 | NT | 0.06 | 0.06 | 1 | 0.25 | 0.25 | 0.5 | 4 | 16 | 0.125 | NT | 0.25 | 0.25 |
| Streptococcus Group D X66 | 64 | 0.06 | 0.25 | 0.5 | 0.5 | 16 | 0.5 | 0.25 | 8 | 0.5 | 2 | 8 | 32 | 64 | 0.5 | 4 | 2 | 1 |
| Streptococcus Group 9960 | 64 | 0.5 | 0.25 | 0.5 | 0.5 | 16 | 0.25 | 0.5 | 8 | 0.5 | 2 | 8 | 32 | 64 | 0.5 | 8 | 2 | 2 |
| Haemophilus influenzae Holt[e] | NT[g] | 1 | 2 | 4 | 4 | 32 | 1 | 1 | NT | 2 | 8 | 16 | 64 | —[h] | 1 | 64 | 8 | 8 |
| Haemophilus influenzae R252[f] | NT | 1 | 2 | 4 | 2 | 32 | 2 | 1 | 1 | 2 | 8 | 16 | 64 | — | 0.5 | 64 | 8 | 8 |
| Shigella sonnei N9 | — | 16 | 64 | 64 | 64 | — | 64 | 32 | — | — | — | — | — | — | 32 | — | — | — |
| Escherichia coli N10 | — | 32 | 64 | — | — | — | 64 | 32 | — | — | — | — | — | — | 32 | — | — | — |
| Escherichia coli EC14 | — | 32 | 64 | — | 64 | — | 64 | 32 | — | — | — | — | — | — | 32 | — | — | — |
| Escherichia coli TEM | — | 8 | 32 | 32 | 32 | — | 16 | 16 | — | 32 | — | — | — | — | 8 | — | 64 | 64 |
| Klebsiella pneumoniae X26 | 64 | 2 | 4 | 8 | 4 | 64 | 4 | 4 | 16 | 8 | 16 | 16 | — | — | 2 | 64 | 16 | 16 |
| Klebsiella pneumoniae KAE | — | 64 | — | — | — | — | — | — | — | — | — | — | — | — | 64 | — | — | — |

[a]Activity = MIC in mcg/ml
[b]Compound numbers from Tables I and III
[c]Penicillin-resistant strain
[d]Methicillin-resistant-strain
[e]Ampicillin-sensitive strain
[f]Ampicillin-resistant strain
[g]NT = not tested
[h]MIC ≧ 128

TABLE VI

Antibiotic Activity of OMT Derivatives[a]

| Test Organism | 2 | 3 | 5 | 7 | 8 | 15 | 17 |
|---|---|---|---|---|---|---|---|
| Klebsiella pneumoniae X68 | 32 | —[c] | — | — | 64 | 64 | — |
| Enterobacter aerogenes C32 | 32 | — | — | — | 64 | 64 | — |
| Enterobacter aerogenes EB17 | 32 | — | — | — | 64 | 64 | — |
| Enterobacter cloacae EB5 | 64 | — | — | — | — | — | — |
| Salmonella heidelberg X514 | 64 | — | — | — | 64 | 64 | — |
| Salmonella typhi 1335 | 64 | — | — | — | 64 | 64 | — |
| Pseudomonas aeruginosa X528 | 16 | 64 | 64 | 32 | 16 | 16 | 64 |
| Pseudomonas aeruginosa X239 | 64 | — | — | — | 64 | 64 | — |
| Pseudomonas aeruginosa Ps18 | 64 | — | — | — | 32 | 32 | — |
| Serratia marcescens X99 | 64 | — | — | — | 64 | 64 | — |
| Serratia marcescens SE3 | 64 | — | — | — | — | — | — |
| Proteus morganii PR15 | 8 | 64 | — | — | 64 | 64 | — |
| Proteus inconstans PR33 | 32 | — | — | — | — | — | — |
| Proteus rettgeri PR7 | 16 | 64 | 64 | — | 32 | 32 | — |
| Proteus rettgeri C24 | 16 | 64 | 64 | 64 | 32 | 32 | — |
| Citrobacter freundii CF17 | 32 | — | — | — | — | — | — |

[a]Activity = MIC in mcg/ml
[b]Compound numbers from Tables I and III; Compounds 1, 4, 6, 9–14 and 16 did not show activity against these strains at the levels tested.
[c]MIC ≧ 128 mcg/ml

TABLE VII

Antibiotic Activity of OMT Derivatives[a]

| Test Organism | 1 | 2 | 3 | 4 | 5 | 6 | 7 | 8 | 9 |
|---|---|---|---|---|---|---|---|---|---|
| Staphylococcus aureus | 50 | 0.39 | 0.78 | 1.56 | 1.56 | 12.5 | 0.39 | ≦0.78 | 12.5 |
| Streptococcus sp. 80 | 12.5 | 0.09 | 0.39 | 0.39 | 1.56 | 6.25 | 0.39 | ≦0.78 | 1.56 |
| Pasteurella multocida 17E[c] | >50 | 1.56 | 6.25 | 6.25 | 6.25 | 25 | 3.12 | 1.56 | 6.25 |
| Pasteurella multocida 60A[d] | >50 | 1.56 | 6.25 | 6.25 | 6.25 | 25 | 3.12 | 3.12 | 6.25 |

TABLE VII-continued

Antibiotic Activity of OMT Derivatives[a]

| Test Organism | Test Compound[b] | | | | | | | | |
|---|---|---|---|---|---|---|---|---|---|
| | | | | | | | | | |
| Pasteurella multocida 22A | >50 | 1.56 | 3.12 | 6.25 | 6.25 | 25 | 1.56 | 1.56 | 25 |
| Pasteurella multocida 40G | >50 | 0.78 | 1.56 | 3.12 | 3.12 | 25 | 0.78 | 1.56 | 12.5 |
| Pasteurella multocida 68C | >50 | 1.56 | 6.25 | 6.25 | 6.25 | 25 | 1.56 | 1.56 | 12.5 |
| Pasteurella hemolytica 22C | >50 | 3.12 | 12.5 | 12.5 | 12.5 | 50 | 6.25 | 6.25 | 12.5 |
| Pasteurella hemolytica 41D | >50 | 1.56 | 6.25 | 12.5 | 12.5 | 50 | 6.25 | 6.25 | 25 |
| Pasteurella hemolytica 23C | >50 | 3.12 | 6.25 | 12.5 | 12.5 | 50 | 6.25 | 6.25 | 12.5 |
| Mycoplasma gallisepticum | 25 | 0.09 | 0.19 | 0.39 | 1.56 | 6.25 | 0.19 | 0.39 | 0.78 |
| Mycoplasma synoviae | 12.5 | 0.39 | 0.39 | 0.78 | 0.78 | 3.12 | ≦0.05 | 0.39 | 0.78 |
| Mycoplasma hyorhinis | 50 | 12.5 | 6.25 | 6.25 | 6.25 | 25 | 6.25 | 3.12 | 12.5 |
| | 10 | 11 | 12 | 13 | 14 | 15 | 16 | 17 | 18 |
| Staphylococcus aureus | 0.78 | 3.12 | 6.25 | 25 | >50 | 1.56 | 12.5 | 3.12 | 6.25 |
| Streptococcus sp. 80 | 0.19 | 0.78 | 6.25 | 6.25 | 25 | ≦0.78 | 6.25 | 1.56 | 1.56 |
| Pasteurella multocida 17E[c] | 3.12 | 6.25 | 12.5 | 50 | >50 | 3.12 | 25 | 6.25 | 12.5 |
| Pasteurella multocida 60A[d] | 3.12 | 12.5 | 12.5 | 50 | >50 | 3.12 | 25 | 12.5 | 12.5 |
| Pasteurella multocida 22A | 25 | 12.5 | 25 | >50 | >50 | 3.12 | 25 | 6.25 | 12.5 |
| Pasteurella multocida 40G | 12.5 | 12.5 | 25 | 50 | >50 | 1.56 | 25 | 6.25 | 12.5 |
| Pasteurella multocida 68C | 1.56 | 6.25 | 25 | 50 | >50 | 3.12 | 25 | 6.25 | 25 |
| Pasteurella hemolytica 22C | 12.5 | 25 | 50 | >50 | >50 | 3.12 | >50 | 25 | 25 |
| Pasteurella hemolytica 41D | 25 | 50 | 50 | >50 | >50 | 3.12 | 50 | 25 | 25 |
| Pasteurella hemolytica 23C | 12.5 | 25 | 50 | >50 | >50 | 6.25 | 50 | 25 | 25 |
| Mycoplasma gallisepticum | 1.56 | 0.78 | 3.12 | 6.25 | 12.5 | 0.09 | 1.56 | 0.78 | 1.56 |
| Mycoplasma synoviae | 0.19 | 0.78 | 3.12 | 12.5 | 6.25 | 0.39 | 12.5 | 1.56 | 3.12 |
| Mycoplasma hyorhinis | 50 | >50 | >50 | 50 | 50 | 0.78 | 12.5 | 25 | 25 |

[a]Activity = MIC in mcg/ml
[b]Compound numbers from Tables I and III
[c]Bovine isolate
[d]Avian isolate The C-23 modified derivatives of OMT of this invention have shown in vivo antimicrobial activity against experimental infections. When two doses of test compound were administered to mice experimentally infected with a gram-positive bacterium, S. pyogenes C203, the activity observed was measured as an $ED_{50}$ value [effective dose in mg/kg to protect 50% of the test animals: see Warren Wick, et al., J. Bacteriol. 81, 233-235 (1961)]. $ED_{50}$ values observed for illustrative compounds are given in Table VIII.

TABLE VIII $ED_{50}$ Values of OMT Derivatives[a]

| | Streptococcus pyogenes C203 | |
|---|---|---|
| Test Compound[b] | Subcutaneous | Oral |
| 2 | 25.7 | >100 |
| 3 | 22.3 | 81 |
| 4 | 12.6 | >100 |
| 5 | 13.7 | >100 |
| 6 | 13.6 | >100 |
| 7 | 21.4 | >100 |
| 8 | 6.3 | >100 |
| 9 | 2.6 | >100 |
| 10 | 5.8 | >100 |
| 12 | 6.2 | >100 |
| 15 | 4.6 | >100 |
| 16 | >30 | >100 |
| 17 | >25 | >100 |

[a]mg/kg × 2; doses given 1 and 4 hours post-infection
[b]Compound numbers from Tables I and III The C-23 modified derivatives of OMT have also shown in vivo antibacterial activity against infections induced by gram-negative bacteria. Table IX summarizes the results of tests in which illustrative compounds were evaluated against Pasteurella infections in one-day-old chicks. The compounds were administered by subcutaneous injection at a dosage of 30 mg/kg, 1 and 4 hours post-challenge of the chicks with Pasteurella multocida (0.1 ml of a twenty-hour tryptose broth culture of an avian P. multocida given subcutaneously). In the tests, all ten non-medicated infected chicks died within 24 hours of Pasteurella challenge.

TABLE IX

Chick Protection with OMT Derivatives[a]

| Test Compound[b] | Pasteurella multocida[c] |
|---|---|
| 2 | 10/10 |
| 3 | 10/10 |
| 4 | 8/10 |
| 5 | 3/10 |
| 7 | 10/10 |
| 8 | 10/10 |
| 9 | 0/10 |
| 10 | 3/10 |
| 11 | 10/10 |
| 12 | 9/10 |
| 13 | 7/10 |
| 14 | 10/10 |

[a]Number of deaths/number treated
[b]Compound numbers from Table I
[c]Administered subcutaneously; 30 mg/kg × 2

This invention also relates to methods of controlling bacterial or mycoplasmal infections. In carrying out the methods of this invention, an effective amount of a compound of formula 1 is administered parenterally to an infected or susceptible warm-blooded animal.

The dose which is effective to control the infection will vary with the severity of the infection and the age, weight, and condition of the animal. The total dose required for protection will generally, however, be in the range of from about 1 to about 100 mg/kg and preferably will be in the range of from about 1 to about 50 mg/kg. Suitable dosage regimens can be constructed.

In another aspect, this invention relates to compositions useful for the control of bacterial or mycoplasmal infections. These compositions comprise a compound of formula 1 together with a suitable vehicle. Such compositions may be formulated for parenteral administration by methods recognized in the art.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

The compounds of formulas 1 and 2 and their acid addition salts can also be used as surface disinfectants. Solutions containing as little as 0.01% by weight are useful for disinfecting purposes. Such solutions, preferably also containing a detergent or other cleansing agent, are useful for disinfecting objects and surfaces where maintenance of sterile conditions is important.

In order to illustrate more fully the operation of this invention, the following examples are provided:

EXAMPLE 1

2'-O-Acetyl-23-deoxy-23-pyridinium-OMT Trifluoro methanesulfonate

A solution of 2'-O-acetyl-OMT (640 mg, 1.0 mmole) and pyridine (0.40 ml, 5.0 mmole) in dichloromethane (10 ml) at 0° C. under argon was treated dropwise with trifluoromethanesulfonic anhydride (0.18 ml, 1.1 mmole). After ten minutes, the reaction appeared incomplete by TLC, and additional trifluoromethanesulfonic anhydride (0.20 ml, 1.2 mmole) was added dropwise. Ten minutes after the addition was completed, the reaction was quenched with saturated sodium bicarbonate solution. The organic layer was separated, dried over sodium sulfate, and filtered. Partial evaporation of the filtrate gave a precipitate which was separated by filtration and air-dried to yield 343 mg (40%) of 2'-O-acetyl-23-deoxy-23-pyridinium-OMT trifluoromethanesulfonate.

EXAMPLE 2

23-Deoxy-23-(phenyl)thio-OMT

A solution of OMT (3.0 g, 5.03 mmole) and s-collidine (2.0 ml, 15.1 mmole) in dichloromethane (110 ml) was cooled to −78° C. under argon and treated dropwise with trifluoromethanesulfonic anhydride (1.2 ml, 7.04 mmole). Ten minutes after the addition was complete, the reaction was warmed to −25° C., and thiophenol (0.75 ml, 7.04 mmole) was added. The cooling bath was removed, and the reaction was allowed to come to room temperature over a one-hour period. The reaction solution was extracted with saturated sodium bicarbonate solution, dried over sodium sulfate, filtered and evaporated. The residue was evaporated again from cyclohexane to give a glass. The glass was purified by silica-gel flash chromatography, eluting with a linear gradient of 1 L of dichloromethane and 1 L of methanol/dichloromethane (15:85) to give 280 mg (8%) of 23-deoxy-23-(phenyl)thio-OMT and 1.97 g of a mixture of unreacted 23-O-trifluoromethanesulfonyl-OMT and 23-deoxy-23-(phenyl)thio-OMT.

EXAMPLE 3

23-Deoxy-23-(acetyl)thio-OMT

A solution of OMT (2.39 g, 4.0 mmole) and s-collidine (2.0 ml, 15.1 mmole) in dichloromethane (50 ml) was cooled to −78° C. under argon and treated dropwise with trifluoromethanesulfonic anhydride (1.05 ml, 6.2 mmole). Ten minutes after the addition was complete, solid potassium thioacetate (460 mg, 4.0 mmole) was added to the reaction, and the cooling bath was removed. Three hours later, additional potassium thioacetate (90 mg, 0.8 mmole) was added to the reaction, and stirring was continued for one hour. The reaction mixture was extracted with saturated sodium bicarbonate solution, dried over sodium sulfate, filtered and evaporated. The residue was evaporated again from cyclohexane to give a glass. The glass was purified by silica-gel flash chromatography, eluting with a linear gradient of 1 L of dichloromethane and 1 L of methanol/dichloromethane (15:85) to give 465 mg (18%) of 23-deoxy-23-(acetyl)thio-OMT and 245 mg (9%) of the elimination-rearrangement product (compound 16).

EXAMPLE 4

23-Deoxy-23-(5-methyl-1,3,4-thiadiazol-2-yl)thio-OMT

A solution of OMT (2.39 g, 4.0 mmole) and s-collidine (2.0 ml, 15.1 mmole) in dichloromethane (40 ml) was cooled to −78° C. under argon and treated dropwise with trifluoromethanesulfonic anhydride (1.0 ml, 6.0 mmole). After fifty minutes, additional trifluoromethanesulfonic anhydride (0.08 ml, 0.5 mmole) was added. One hour later, 2-mercapto-5-methyl-thiadiazole (581 mg, 4.4 mmole) was added to the reaction. The cooling bath was removed, and the reaction was allowed to come to room temperature over a two-hour period. The reaction mixture was extracted with saturated sodium bicarbonate solution (50 ml), dried over sodium sulfate, filtered and evaporated. The residue was evaporated again from cyclohexane to give a glass. The glass was purified by silica-gel flash chromatography, eluting with dichloromethane and then with dichloromethane containing increasing percentages of methanol (0→15%) to give 1.3 g (46%) of 23-deoxy-23-(5-methyl-1,3,4-thiadiazol-2-yl)thio-OMT.

EXAMPLE 5

23-Deoxy-23-(1-methyltetrazol-5-yl)thio-OMT

Following the procedure of Example 4, OMT (2.39 g, 4.0 mmole) and s-collidine (2.0 ml, 15.1 mmole) were reacted with trifluoromethanesulfonic anhydride (1.05 ml, 6.2 mmole) and then with 5-mercapto-1-methyltetrazole (511 mg, 4.4 mmole). The resulting crude product was purified by silica-gel flash chromatography, eluting with a linear gradient of 1 L of dichloromethane and 1 L of methanol/dichloromethane (15:85) to give 1.33 g (48%) of 23-deoxy-23-(1-methyltetrazol-5-yl)thio-OMT.

EXAMPLE 6

23-Deoxy-23-(5-methyl-1,3,4-oxadiazol-2-yl)-OMT

Following the procedure of Example 4, OMT (2.39 g, 4.0 mmole) and s-collidine (2.0 ml, 15.1 mmole) were reacted with trifluoromethane sulfonic anhydride (1.05 ml, 6.2 mmole) and then with 2-mercapto-5-methyloxadiazole (511 mg, 4.4 mmole). The resulting crude product was purified by silica-gel chromatography (Waters Prep 500). Elution with a linear gradient of 4 L of dichloromethane and 4 L of methanol/dichloromethane (15:85) yielded 1.70 g (61%) of 23-deoxy-23-(5-methyl-1,3,4-oxadiazol-2-yl)-OMT.

EXAMPLE 7

23-Deoxy-23-azido-OMT

Following the procedure of Example 4, OMT (20.0 g, 33.5 mmole) and s-collidine (9.0 ml, 67 mmole) were reacted with trifluoromethanesulfonic anhydride (8.4 ml, 50.0 mmole) and then with lithium azide (3.3 g, 67 mmole). The cooling bath was removed; and after thirty minutes, the reaction mixture was diluted with acetonitrile to bring the lithium azide into solution. After two hours, the solution was evaporated to dryness, dissolved in dichloromethane and worked up as usual. The crude product was purified by silica-gel chromatography (Waters Prep 500). Elution with a linear gradient of 4 L of dichloromethane and 4 L of methanol/dichloromethane (5:95), adding 100 ml of methanol to the latter solution after elution volumes of 3 and 5 L, yielded 12.0 g (58%) of 23-deoxy-23-azido-OMT.

EXAMPLE 8

23-Deoxy-23-amino-OMT

A solution of 23-deoxy-23-azido-OMT (12.0 g, 19.3 mmole), triphenylphosphine (5.3 g, 20.3 mmole) and water (0.37 ml, 20.3 mmole) in distilled tetrahydrofuran (200 ml) was stirred at room temperature for four days. The solution was evaporated to give a glass which was partitioned between ethyl acetate and 0.1M acetic acid solution. The aqueous layer was separated, washed with ethyl acetate and carefully poured into saturated sodium bicarbonate solution. The resulting mixture was extracted with dichloromethane. The extract was dried over sodium sulfate, filtered and evaporated to give 10.5 g (91%) of 23-deoxy-23-amino-OMT.

EXAMPLE 9

23-Deoxy-23-N-(phenylacetyl)amino-OMT

A solution of 23-amino-OMT (900 mg, 1.5 mmole) in 10% aqueous acetone (50 ml) was treated with N-phenylacetyloxy-succinimide (352 mg, 1.5 mmole) and stirred at room temperature for two hours. After the addition of a few drops of methanol, the reaction mixture was evaporated to an aqueous solution and then was extracted with dichloromethane. The dichloromethane extract was extracted with saturated sodium bicarbonate solution, dried over sodium sulfate, and filtered. The filtrate was evaporated to give a glass. The glass was purified by silica-gel flash chromatography, eluting with a linear gradient of 500 ml of dichloromethane and 500 ml of methanol/dichloromethane (1:3) to give 487 mg (45%) of 23-deoxy-23-(phenylacetyl)amino-OMT.

EXAMPLE 10

23-Deoxy-23-[(D)-(−)-(N-t-BOC-phenylglycyl)amino]-OMT

Following the procedure of Example 9, 23-deoxy-23-amino-OMT (3.0 g, 5.0 mmole) and N-(D)-(−)-t-BOC-phenylglycyloxy)-succinimide (1.752 g, 5.0 mmole) were reacted to give a crude product. This product was purified by silica-gel flash chromatography, eluting with a linear gradient of 1 L of dichloromethane and 1 L of methanol/dichloromethane (1:4) to give 2.5 g (60%) of 23-deoxy-23-[(D)-(−)-(N-t-BOC-phenylglycyl)amino]-OMT.

EXAMPLE 11

23-Deoxy-23-N-(D-(−)-phenylglycyl)amino-OMT bis(trifluoroacetate) salt

23-Deoxy-23-(N-t-BOC-phenylglycyl)amino-OMT (1.0 g, 1.2 mmole) was dissolved in trifluoroacetic acid (10 ml) at 0° C. and stirred for thirty minutes. The reaction mixture was diluted with diethyl ether. The resulting precipitate was collected on a filter, washed with n-hexane and air dried to give a quantitative yield of 23-deoxy-23-N-(D-(−)-phenylglycyl)amino-OMT bis(trifluoroacetate) salt as a tan powder.

EXAMPLE 12

23-Deoxy-23-fluoro-OMT

A solution of OMT (2.39 g, 4.0 mmole) and s-collidine (1.6 ml, 12.0 mmole) in dichloromethane (50 ml) was cooled to −78° C. under argon and treated dropwise with trifluoromethanesulfonic anhydride (1.0 ml, 6.0 mmole). Ten minutes after the addition was complete, solid tetraethylammonium fluoride dihydrate (1.48 g, 8.0 mmole) was added to the reaction. The cooling bath was removed, and the reaction was allowed to come to room temperature over a two-hour period. The reaction mixture was extracted with saturated sodium bicarbonate solution, dried over sodium sulfate, filtered and evaporated. The residue was evaporated again from cyclohexane to give a glass which was purified by silica-gel chromatography (Waters Prep 500). Elution with a linear gradient of 4 L of dichloromethane and 4 L of methanol/dichloromethane (15:85) yielded 520 mg (22%) of 23-deoxy-23-fluoro-OMT.

EXAMPLE 13

Elimination-Rearrangement Product (Compound 16)

A solution of OMT (2.39 g, 4.0 mmole) and s-collidine (1.5 ml, 11.3 mmole) in dichloromethane (40 ml) was cooled to −78° C. under argon and treated dropwise with trifluoromethanesulfonic anhydride (1.05 ml, 6.2 mmole). Ten minutes after the addition had been completed, the reaction mixture was treated with diazabicycloundecene (66.9 mg, 4.4 mmole). The cooling bath was removed, and the reaction was allowed to come to room temperature over a two-hour period. The reaction mixture was worked up as in Example 12 to give a glass. The glass was purified by silica-gel flash chromatography, eluting with a linear gradient of 1 L of dichloromethane and 1 L of methanol/dichloromethane (15:85) to give 475 mg (20.5%) of the elimination-rearrangement product (Compound 16).

EXAMPLE 14

Methanol-rearrangement Product (Compound 17)

A solution of OMT (6.0 g, 10.05 mmole) and s-collidine (4.0 ml, 30.0 mmole) in dichloromethane (150 ml) was cooled to −78° C. under argon and treated dropwise with trifluoromethanesulfonic anhydride (2.4 ml, 14.07 mmole). Five minutes after the addition had been completed, the reaction mixture was allowed to warm to 0° C. A portion (40 ml, 2.5 mmole theoretical) of this reaction solution was transferred to another flask and treated with methanol (1.0 ml, excess) at room temperature under argon. After being stirred for five hours, the reaction mixture was worked up as in Example 13; elution with a linear gradient of 600 ml of dichloromethane and 600 ml of methanol/dichloromethane (1:9) gave 440 mg (29%) of compound 17.

EXAMPLE 15

Phenethanol-rearrangement Product (Compound 18)

Using the procedure of Example 14, 23-O-trifluoromethanesulfonyl-OMT solution (40 ml, 2.5 mmole theory) was reacted with phenethyl alcohol (2 ml, excess) at room temperature under argon. The reaction mixture was stirred for five hours and worked up as in Example 13. Elution with a linear gradient of 700 ml of dichloromethane and 700 ml of methanol/dichloromethane (1:9) gave 500 mg (29%) of compound 18.

EXAMPLE 16

23-Deoxo-23-(1H-5,6-dioxo-4-methyl-1,2,4-triazin-3-yl)thio-OMT

In a manner similar to that of Example 5, OMT (2.39 g, 4.0 mmole) was reacted with trifluoromethanesulfonic anhydride (1.05 ml, 6.2 mmole) and then with 1H-5,6-dioxo-4-methyl-1,2,4-triazin-3-thiol (700 mg, 4.4 mmole); acetonitrile was added to give a solution. After two hours, the reaction mixture was evaporated to an oil which was dissolved in a mixture of dichloromethane/ethyl acetate/acetonitrile. This solution was washed with saturated sodium bicarbonate solution, dried over sodium sulfate, filtered and evaporated to give an oil which was dissolved in acetonitrile. The product was precipitated by the addition of dichloromethane:n-hexane (8:1) and separated to give 1.59 g (54%) of 23-deoxo-23-(1H-5,6-dioxo-4-methyl-1,2,4-triazin-3-yl)thio-OMT.

EXAMPLE 17

Alternate procedure for 23-deoxy-23-amino-OMT

A solution of 23-deoxy-23-azido-OMT (622 mg, 1.0 mmole) in degassed 20% aqueous methanol (25 ml) was treated with solid chromous chloride (290 mg, 2.4 mmole) under argon. After being stirred for thirty minutes, additional chromous chloride (135 mg, 1.1 mmole) was added. A final addition of chromous chloride (90 mg, 0.7 mmole) was made after another ten minutes. Thirty minutes after the last addition, the reaction mixture was evaporated to an aqueous solution which was diluted with saturated sodium bicarbonate solution and filtered through a celite pad. The filtrate was extracted with ethyl acetate. The combined ethyl acetate extracts were dried over sodium sulfate, filtered and evaporated to give 350 mg (59%) of 23-deoxy-23-amino-OMT as a colorless solid.

EXAMPLE 18

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

We claim:

1. A compound of the formula

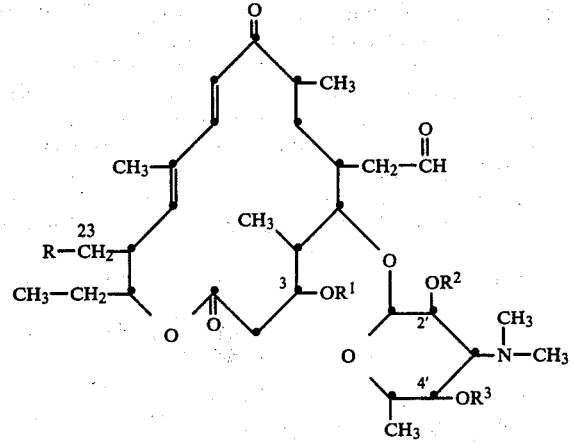

wherein

R is chloro, fluoro, $-S-R^4$, azido, $-NHR^5$, pyridinium or $-OSO_2CF_3$;

$R^1$ is hydrogen, $C_1-C_5$-alkanoyl; $C_1-C_5$-alkanoyl having from one to three halo substituents; benzoyl, phenylacetyl, phenylpropionyl, phenoxyacetyl or phenylthioacetyl; or benzoyl, phenylacetyl, phenylpropionyl, phenoxyacetyl or phenylthioacetyl having on the phenyl ring from one to five halo or methyl or from one to two methoxyl, nitro or hydroxyl groups;

$R^2$ and $R^3$ are hydrogen, $C_1-C_5$-alkanoyl; $C_1-C_5$-alkanoyl having from one to three halo substituents; benzoyl, phenylacetyl or phenylpropionyl; or benzoyl, phenylacetyl or phenylpropionyl having on the phenyl ring from one to five halo or methyl or from one to two methyl, nitro or hydroxyl groups;

$R^4$ is hydrogen, $C_1-C_6$-alkyl, cyclohexyl, $C_1-C_5$-alkanoyl, phenyl or benzyl, phenyl or benzyl having on the phenyl ring from one to five halo or methyl or from one to two methyl, nitro or hydroxyl groups; a heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; or a specified heteroaryl group having a $C_1-C_4$-alkyl, methoxy, ethoxy, hydroxy, keto, phenyl, halophenyl, methylphenyl, or methoxyphenyl substituent; and $R^5$ is hydrogen or an acyl group selected from $C_1-C_5$-alkanoyl; $C_1-C_5$-alkanoyl having from one to three halo substituents; benzoyl, phenylacetyl, or phenylpropionyl; or benzoyl, phenylacetyl or phenylpropionyl having on the phenyl ring from one to five halo or methyl or from one to two methyl, nitro or hydroxyl groups; phenylglycyl or phenylalanyl; or phenylglycyl or phenylalanyl or amino-protected phenylglycyl or phenylalanyl;

and the acid addition salts thereof.

2. A compound of claim 1 wherein R is chloro.
3. A compound of claim 1 wherein R is fluoro.
4. A compound of claim 1 wherein R is —S—$R^4$.
5. A compound of claim 4 wherein $R^4$ is phenyl or phenyl having on the phenyl ring from one to five halo or methyl or from one to two methyl, nitro or hydroxyl groups.
6. A compound of claim 5 wherein $R^4$ is phenyl.
7. A compound of claim 4 wherein $R^4$ is $C_1-C_6$-alkyl.
8. A compound of claim 4 wherein $R^4$ is acetyl.
9. A compound of claim 4 wherein $R^4$ is a specified heteroaryl group or a specified heteroaryl group having a $C_1-C_4$-alkyl, methoxy, ethoxy, hydroxy, keto, phenyl, halophenyl, methylphenyl, or methoxyphenyl substituent.
10. A compound of claim 9 wherein $R^4$ is tetrazolyl.
11. A compound of claim 10 wherein $R^4$ is 1-methyltetrazol-5-yl.
12. A compound of claim 9 wherein $R^4$ is thiadiazolyl.
13. A compound of claim 12 wherein $R^4$ is 5-methyl-1,3,4-thiadiazol-2-yl.
14. A compound of claim 9 wherein $R^4$ is oxadiazolyl.
15. A compound of claim 14 wherein $R^4$ is 5-methyl-1,3,4-oxadiazol-2-yl.
16. A compound of claim 9 wherein $R^4$ is triazinyl.
17. A compound of claim 16 wherein $R^4$ is 1,2,4-triazin-3-yl.
18. A compound of claim 16 wherein $R^4$ is 1-H-5,6-dioxo-4-methyl-1,2,4-triazin-3-yl.
19. A compound of claim 1 wherein R is pyridinium.
20. A compound of claim 1 wherein R is azido.
21. A compound of claim 1 wherein R is —$NHR^5$.
22. A compound of claim 21 wherein $R^5$ is hydrogen.
23. A compound of claim 21 wherein $R^5$ is $C_1-C_5$-alkanoyl or $C_1-C_5$-alkanoyl having from one to three halo substituents.
24. A compound of claim 23 wherein $R^5$ is acetyl.
25. A compound of claim 21 wherein $R^5$ is benzoyl, phenylacetyl, or phenylpropionyl; or benzoyl, phenylacetyl or phenylpropionyl having on the phenyl ring from one to five halo or methyl or from one to two methyl, nitro or hydroxyl groups.
26. A compound of claim 25 wherein $R^5$ is phenylacetyl.
27. A compound of claim 21 wherein $R^5$ is phenylglycyl.
28. A compound of claim 1 wherein R is —$OSO_2CF_3$.
29. A compound of the formula

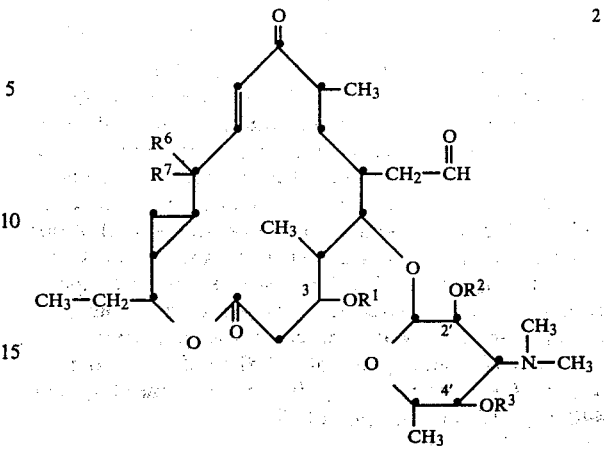

wherein:
$R^1$ is hydrogen, $C_1-C_5$-alkanoyl; $C_1-C_5$-alkanoyl having from one to three halo substituents; benzoyl, phenylacetyl, phenylpropionyl, phenoxyacetyl or phenylthioacetyl; or benzoyl, phenylacetyl, phenylpropionyl, phenoxyacetyl or phenylthioacetyl having on the phenyl ring from one to five halo or methyl or from one to two methyl, nitro or hydroxyl groups;

$R^2$ and $R^3$ are hydrogen, $C_1-C_5$-alkanoyl; $C_1-C_5$-alkanoyl having from one to three halo substituents; benzoyl, phenylacetyl or phenylpropionyl; or benzoyl, phenylacetyl or phenylpropionyl having on the phenyl ring from one to five halo or methyl or from one to two methyl, nitro or hydroxyl groups;

$R^6$ and $R^7$ together form a $CH_2=$ group or $R^6$ is $R^8O$— and $R^7$ is methyl; and $R^8$ is $C_1-C_4$ alkyl, benzyl or phenethyl; and the acid addition salts thereof.

30. A compound of claim 29 wherein $R^6$ and $R^7$ together form a $CH_2=$ group.
31. A compound of claim 29 wherein $R^6$ is $R^8O$—.
32. A compound of claim 31 wherein $R^8$ is methyl.
33. A compound of claim 31 wherein $R^8$ is phenethyl.
34. A compound of claim 2, 3, 4, 5, 7, 8, 9, 10, 12, 14, 16, 19, 20, 21, 28 or 29 wherein $R^1$, $R^2$, and $R^3$ are hydrogen.
35. A compound of claim 2, 3, 4, 5, 7, 8, 9, 10, 12, 14, 16, 19, 20, 21, 28 or 29 wherein $R^2$ and $R^3$ are $C_1-C_5$-alkanoyl or $C_1-C_5$-alkanoyl having from one to three halo substituents.
36. A compound of claim 35 wherein $R^2$ and $R^3$ are acetyl.
37. A compound of claim 2, 3, 4, 5, 7, 8, 9, 10, 12, 14, 16, 19, 20, 21, 28 or 29 wherein $R^1$ is benzoyl, phenylacetyl, phenylpropionyl, phenoxyacetyl or phenylthioacetyl or benzoyl, phenylacetyl, phenylpropionyl, phenoxyacetyl or phenylthioacetyl having on the phenyl ring from one to five halo or methyl or from one to two methyl, nitro or hydroxyl groups.
38. A compound of claim 37 wherein $R^1$ is phenylacetyl.
39. A composition useful for the treatment of bacterial or mycoplasmal infections comprising an effective amount of a compound of claim 1, 2, 3, 4, 20, 21 or 29 or a pharmaceutically acceptable acid addition salt thereof and a suitable pharmaceutical vehicle.

40. A method for treating infections caused by gram-positive bacteria which comprises administering to an infected or susceptible warm-blooded animal an amount of a composition of claim 39 which is effective against said infection.

41. A method for treating infections caused by gram-negative bacteria which comprises administering to an infected or susceptible warm-blooded animal an amount of a composition of claim 39 which is effective to treat said infection.

42. A method of claim 41 wherein the gram-negative bacterium is a Pasteurella species.

43. A method for treating infections caused by Mycoplasma species which comprises administering parenterally to an infected or susceptible warm-blooded animal an amount of a composition of claim 39 which is effective against the Mycoplasma species.

* * * * *

UNITED STATES PATENT AND TRADEMARK OFFICE
CERTIFICATE OF CORRECTION

PATENT NO. : 4,459,290

DATED : July 10, 1984

INVENTOR(S) : Herbert A. Kirst and John E. Toth

It is certified that error appears in the above—identified patent and that said Letters Patent is hereby corrected as shown below:

Column 18, line 60, "methyl" should read -- methoxyl --; line 65, "two methyl" should read -- two methoxyl --.

Column 19, line 12, "two methyl" should read -- two methoxyl --; line 22, "two methyl" should read -- two methoxyl --; line 62, "methyl" should read -- methoxyl --.

Column 20, line 27, "two methyl" should read -- two methoxyl --; line 35, "methyl" should read -- methoxyl --; line 61, "methyl" should read -- methoxyl -

Signed and Sealed this

Eleventh Day of March 1986

[SEAL]

Attest:

DONALD J. QUIGG

Attesting Officer     Commissioner of Patents and Trademarks